United States Patent
Hughes et al.

(10) Patent No.: US 12,241,947 B2
(45) Date of Patent: *Mar. 4, 2025

(54) LASER BONDED GLASS-SILICON VAPOR CELL

(71) Applicant: FieldLine Inc., Boulder, CO (US)

(72) Inventors: Kenneth J. Hughes, Lafayette, CO (US); Collin Coolidge, Erie, CO (US)

(73) Assignee: FieldLine Inc., Boulder, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/533,365

(22) Filed: Dec. 8, 2023

(65) Prior Publication Data

US 2024/0111000 A1 Apr. 4, 2024

Related U.S. Application Data

(63) Continuation of application No. 17/877,565, filed on Jul. 29, 2022, now Pat. No. 11,867,776.

(60) Provisional application No. 63/227,742, filed on Jul. 30, 2021.

(51) Int. Cl.
*G01R 33/00* (2006.01)
*C03B 23/20* (2006.01)
*G01R 33/032* (2006.01)

(52) U.S. Cl.
CPC .......... *G01R 33/0052* (2013.01); *C03B 23/20* (2013.01); *G01R 33/032* (2013.01)

(58) Field of Classification Search
CPC .. G01R 33/0052; G01R 33/032; G01R 33/26; A61B 5/245; A61B 5/25; C03C 27/10; C03B 23/20

USPC ....................................................... 324/244.1
See application file for complete search history.

(56) References Cited

U.S. PATENT DOCUMENTS 10,605,840 B1 * 3/2020 Amarloo ............ G01R 29/0885
2021/0114926 A1 * 4/2021 Ramirez-Serrano ........................
G01R 29/0864

OTHER PUBLICATIONS

Kwon, Jin Gu, et al. "Study on Reliability of Vapor Cell by Laser Packaging with Au/Au-Sn Heterojunction." Journal of the Korean Institute of Electrical and Electronic Material Engineers 33.5 (2020): 367-372. (Year: 2020).*

Chang, Zhang, et al. "Micro Rb atomic vapor cells for the chip-scale atomic clock." 2014 IEEE International Frequency Control Symposium (FCS). IEEE, 2014. (Year: 2014).*

(Continued)

*Primary Examiner* — Christopher P McAndrew

(57) ABSTRACT

Various embodiments comprise a laser bonded glass-silicon vapor cell for performing spectroscopy on particles like atoms or molecules. In some examples, the laser bonded glass-silicon vapor cell comprises a glass base, a glass top, a silicon piece, and a filling material. The silicon piece comprises at least one through hole. The lower surface of the silicon piece is hermetically bonded to the glass base. The upper surface of the silicon piece is laser bonded to the glass top. The filling material is positioned in a cavity formed by the through hole, the glass base, and the glass top. The filling material may comprise an alkali metal, a salt slush, or an inert gas. In some examples the cavity formed by the through hole, the glass base, and the glass top may comprise a vacuum encapsulation.

20 Claims, 11 Drawing Sheets

(56) References Cited

OTHER PUBLICATIONS

Karlen, Sylvain. Fabrication and characterization of MEMS alkali vapor cells used in chip-scale atomic clocks and other atomic devices. Université de Neuchâtel, Faculté des sciences, 2017. (Year: 2017).*

Chutani, Ravinder. Design, Technology and Packaging of Cesium Vapor Cells for MEMS Atomic Clocks. Diss. Universite de Franche-Comte, 2011. (Year: 2011).

Knappe, Svenja, et al. "Atomic vapor cells for miniature frequency references." IEEE International Frequency Control Symposium and PDA Exhibition Jointly with the 17th European Frequency and Time Forum, 2003. Proceedings of the 2003. IEEE, 2003. (Year: 2003).

* cited by examiner

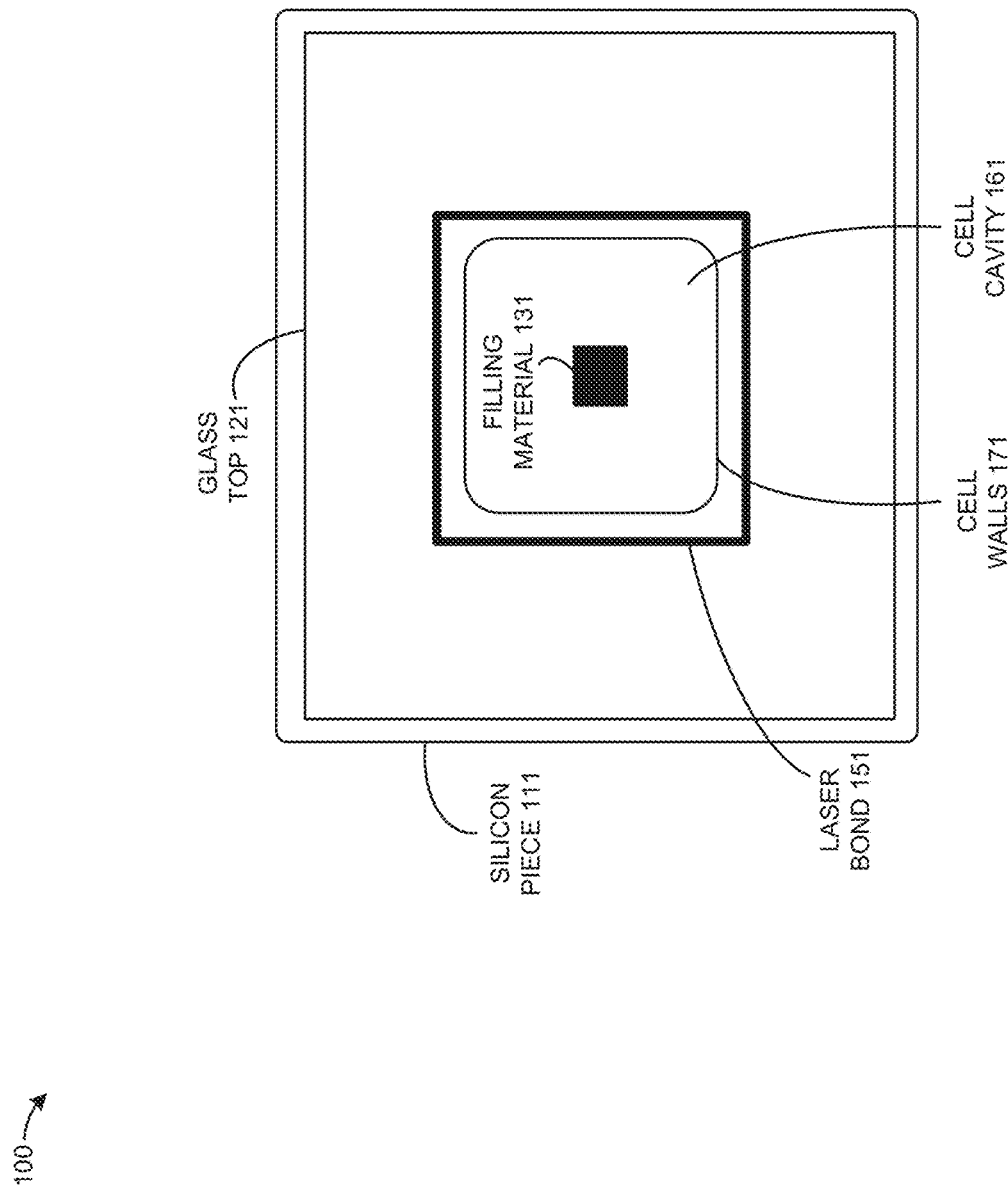

LASER BONDED GLASS-SILICON VAPOR CELL

RELATED APPLICATIONS

This U.S. patent application is a continuation of and claims priority to U.S. patent application Ser. No. 17/877,565 titled, "LASER BONDED GLASS-SILICON VAPOR CELL" which was filed on Jul. 29, 2022, which in turn claims the benefit of and priority to U.S. Provisional Patent Application 63/227,742 titled, "LASER WELDED GLASS SILICON VAPOR CELL FOR AN OPTICALLY PUMPED MAGNETOMETER" which was filed on Jul. 30, 2021. Both U.S. patent application Ser. No. 17/877,565 and U.S. Provisional Patent Application 63/227,742 are hereby incorporated by reference into this U.S. patent application in their entirety.

BACKGROUND

Glass vapor cells are devices configured to perform spectroscopy on atoms and molecules. Exemplary uses of glass vapor cells include performing magnetoencephalography to detect magnetic field generated by neuronal activity. Glass vapor cells comprise a glass capsule that houses a filling material. Glass vapor cells are constructed by creating a glass cavity and depositing a filling material like an alkali metal into the glass cavity in an inert environment like a vacuum. The glass cavity is heated and pinched off to fully encapsulate the filling material within the glass cavity. Unfortunately, the glass vapor cells are inefficient and difficult to construct. Moreover, the construction process of glass vapor cells cannot be effectively and efficiently scaled.

Other types of vapor cells for performing spectroscopy on atoms and molecules comprise hybrid glass-silicon vapor cells. The glass-silicon vapor cells comprise a capsule that houses a filling material where the silicon forms the walls of the capsule, and the glass forms the base and top of the capsule. Glass-silicon vapor cells are constructed by anodically bonding the silicon to the glass to encapsulate the filling material like an alkali metal. The anodic bonding process used to construct the glass-silicon vapor cells inefficiently requires an elevated temperature. The elevated temperature results in undesired chemical reactions that alter the chemical composition of the filling material. Moreover, the elevated temperature may cause the filling material to diffuse into the glass. The diffusion results in a decrease of cell pressure and a change in the composition of the glass. Unfortunately, the anodic bonding process does not efficiently and effectively construct glass-silicon vapor cells. Moreover, the decrease in cell pressure, altered composition of the glass, and undesired chemical reactions may negatively impact the use of the glass-silicon vapor cell.

OVERVIEW

This Overview is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

Various embodiments of the present technology relate to solutions for the manufacture and use of vapor cells for atomic spectroscopy. In some embodiments, a laser bonded glass-silicon vapor cell for performing spectroscopy on particles like atoms or molecules is disclosed. In some examples, the laser bonded glass-silicon vapor cell comprises a glass base, a glass top, a silicon piece, and a filling material. The silicon piece comprises at least one through hole. The lower surface of the silicon piece is hermetically bonded to the glass base. The upper surface of the silicon piece is laser bonded to the glass top. The filling material is positioned in a cavity formed by the through hole, the glass base, and the glass top. The filling material may comprise an alkali metal, a salt slush, or an inert gas. In some examples the cavity formed by the through hole, the glass base, and the glass top may comprise a vacuum encapsulation.

In some embodiments, a method of manufacturing a laser bonded glass-silicon vapor cell for performing spectroscopy on particles like atoms or molecules is disclosed. The method comprises making a through hole in a silicon piece. The method continues by hermetically bonding a lower surface of the silicon piece to a glass base. The method continues by positioning a filling material in the through hole of the silicon piece on the glass base. The method continues by clamping a glass top to the silicon piece to contact the glass top with an upper surface of the silicon piece. The method continues by laser bonding the upper surface of the silicon piece to the glass top. The method continues by removing the clamping.

DESCRIPTION OF THE DRAWINGS

Many aspects of the disclosure can be better understood with reference to the following drawings. The components in the drawings are not necessarily drawn to scale. Moreover, in the drawings, like reference numerals designate corresponding parts throughout the several views. While several embodiments are described in connection with these drawings, the disclosure is not limited to the embodiments disclosed herein. On the contrary, the intent is to cover all alternatives, modifications, and equivalents.

FIG. 2A illustrates an example of a laser bonded glass-silicon vapor cell.

Figure 1:
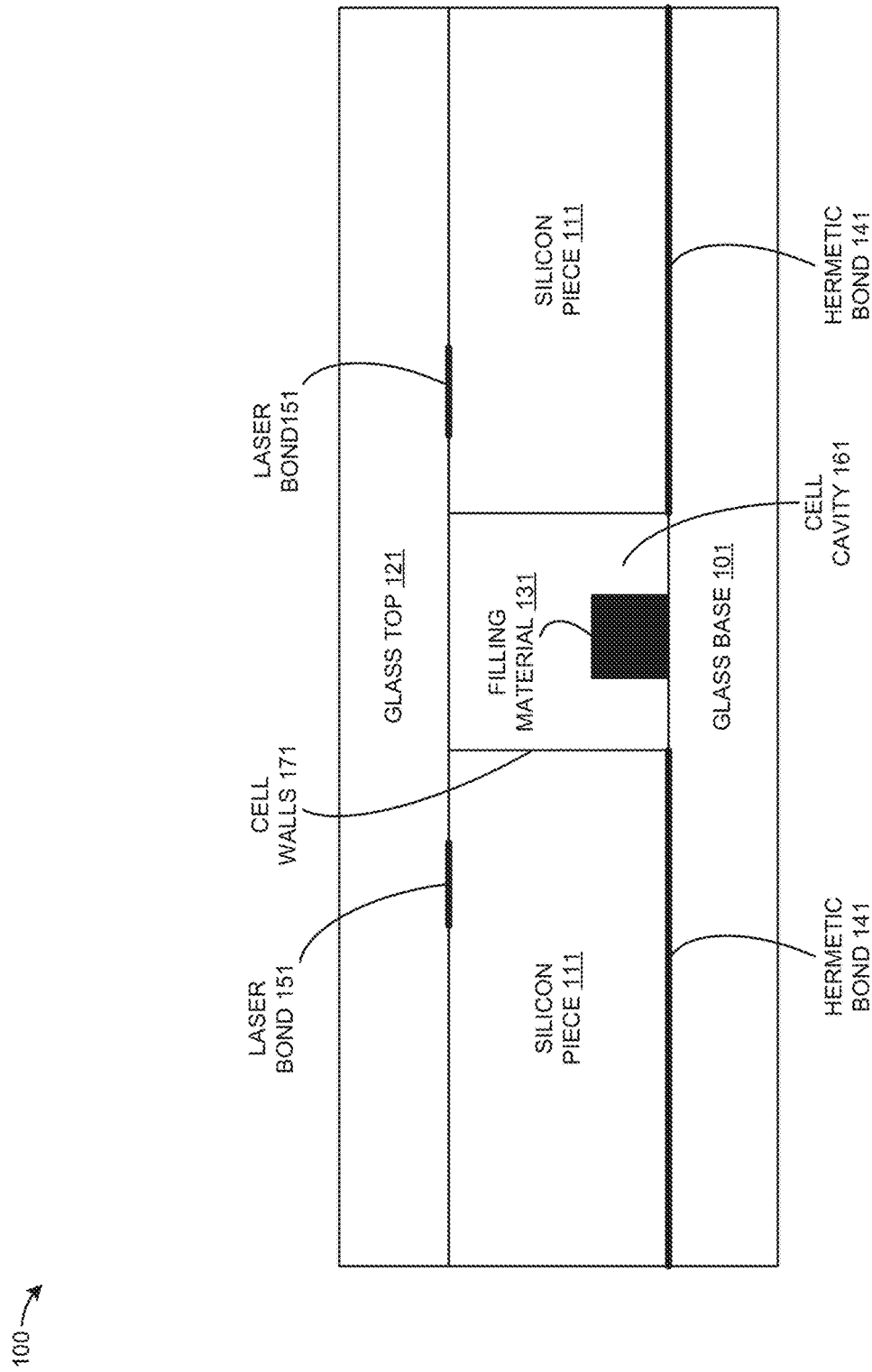
FIG. 1 illustrates an example of a laser bonded glass-silicon vapor cell.

The drawings have not necessarily been drawn to scale. Similarly, some components or operations may not be separated into different blocks or combined into a single block for the purposes of discussion of some of the embodiments of the present technology. Moreover, while the technology is amendable to various modifications and alternative forms, specific embodiments have been shown by way of example in the drawings and are described in detail below. The intention, however, is not to limit the technology to the particular embodiments described. On the contrary, the technology is intended to cover all modifications, equivalents, and alternatives falling within the scope of the technology as defined by the appended claims.

DETAILED DESCRIPTION

The following description and associated figures teach the best mode of the invention. For the purpose of teaching inventive principles, some conventional aspects of the best mode may be simplified or omitted. The following claims specify the scope of the invention. Note that some aspects of the best mode may not fall within the scope of the invention as specified by the claims. Thus, those skilled in the art will appreciate variations from the best mode that fall within the scope of the invention. Those skilled in the art will appreciate that the features described below can be combined in various ways to form multiple variations of the invention. As a result, the invention is not limited to the specific examples described below, but only by the claims and their equivalents.

Various embodiments of the present technology relate to laser bonded glass-silicon vapor cells. More specifically, embodiments of the present technology relate to systems and methods for constructing laser bonded glass-silicon vapor cells for use in particle spectroscopy. Now referring to the Figures.

FIG. 1 illustrates a two-dimensional cross section view of laser bonded glass-silicon vapor cell 100. Laser bonded glass-silicon vapor cell 100 is a vapor cell configured to perform spectroscopy on atoms and molecules. For example, laser bonded glass-silicon vapor cell 100 may be used to perform magnetoencephalography to detect and characterize a magnetic field generated by neuronal activity of a human brain. Laser bonded glass-silicon vapor cell 100 comprises glass base 101, silicon piece 111, glass top 121, filling material 131, hermetic bond 141, laser bond 151, cell cavity 161, and cell walls 171. Silicon piece 111 may comprise a portion of a silicon wafer. For example, silicon piece 111 may be cut out of a silicon wafer to construct laser bonded glass-silicon vapor cell. In some examples, silicon piece 111 may comprise an entire silicon wafer. Silicon piece 111 may be replaced by a different type of material that can hermetically bond to glass and that does not react, mildly reacts, or undergoes a desired chemical reaction with filling material 131. In this example, laser bonded glass-silicon vapor cell 100 comprises a rectangular shape, however the shape of vapor cell 100. Silicon piece 111 comprise a through hole that passes through silicon piece 111 to form cell walls 171. Cell walls 171 typically run perpendicular to the horizontal axis of silicon piece 111. For example, a drilling tool may bore entirely through silicon piece 111 to create a through hole.

Silicon piece 111 is positioned between glass base 101 and glass top 121. Glass base 101 and glass top 121 are transparent to laser light. Glass base 101 and glass top 121 may comprise low-thermal-expansion borosilicate glass, aluminosilicate glass, or another type of glass or transparent material that can hermetically bond to silicon piece 111. Glass base 101 and glass top 121 are transparent to laser light. For example, laser bonded glass-silicon vapor cell 100 may be used in an Optically Pumped Magnetometer (OPM) and lasers light emitted from lasers in the OPM may pass through glass base 101 and glass top 121 to interact with filling material 131. In some examples, glass base 101 and glass top 121 may comprise an anti-reflective coating positioned on their surfaces. For example, anti-reflective coating may be positioned on their outer surfaces opposite their surfaces contacting silicon piece 111. The anti-reflective coating inhibits laser light from reflecting off of the surfaces of glass base 101 and glass top 121. The anti-reflective coating may comprise aluminum oxide, titanium oxide, or another type of anti-reflective material that forms a thin film layer deposited on the outer surfaces of glass base 101 and glass top 121. In some examples, glass base 101 and glass top 121 may be fully coated in the anti-reflective coating. In some examples, the anti-reflective coating may be patterned and only partially cover glass base 101 and glass top 121.

The lower surface of silicon piece 111 is bonded to the upper surface of glass base 101 by hermetic bond 141. Hermetic bond 141 may comprise an anodic bond, a laser bond, a hybrid anodic/laser bond, or some other type of bond that hermetically binds silicon piece 111 to glass base 101. The upper surface of silicon piece 111 is bonded to the lower surface of glass top 121 by laser bond 151. For example, a laser may be applied to glass top 121 and silicon piece 111 to create laser bond 151. Laser bond 151 may comprise two bond types. The first bond type may comprise a laser weld where the upper surface of silicon piece and the lower surface of the glass top 121 melt into each other. The second bond type may comprise a laser induced ion diffusion bond that hermetically contacts silicon piece 111 and glass top 151. In some examples, laser bond 151 comprises a hybrid anodic/laser bond. Glass base 101, glass top 121, hermetic bond 141, laser bond 151, and cell walls 171 form a hermetic seal that encapsulates cell cavity 161. The exposed area of glass base 101 and glass top 121 form windows that allow light to enter and pass-through cell cavity 161.

Filling material 131 is positioned on the upper surface of glass base 101 within cell cavity 161. Filling material 131 may comprise an alkali metal, alkali slush, a salt slush, an inert gas, a vacuum encapsulation, and/or some other type of filling material. The alkali metal may comprise a metal like rubidium. The alkali slush may comprise an alkali salt and azide mixture like rubidium azide. The alkali slush may comprise an alkali azide like rubidium azide. The inert gas may comprise an inert like nitrogen or helium. The vacuum encapsulation may comprise a volume of low-pressure contained within cell cavity 161. It should be appreciated that the material type of filling material 131 depends in part on the intended use for laser bonded glass-silicon vapor cell 100. For example, if laser bonded glass-silicon vapor cell 100 is used in an OPM, filling material 131 may comprise rubidium metal and an inert gas. When assembled, filling material 131 may partially or fully sublimate and fill cell cavity 161 with the sublimated vapors. For example, filling material 131 may comprise rubidium metal and the rubidium metal may sublimate to fill cell cavity 161 with rubidium vapors. Advantageously, the laser bonded glass-silicon vapor cell 100 can be efficiently constructed. Moreover, the laser bonding process hermetically bonds glass top 121 to silicon piece 111 without excessively heating laser bonded glass-silicon vapor cell 100 to an elevated temperature.

Figure 2B:
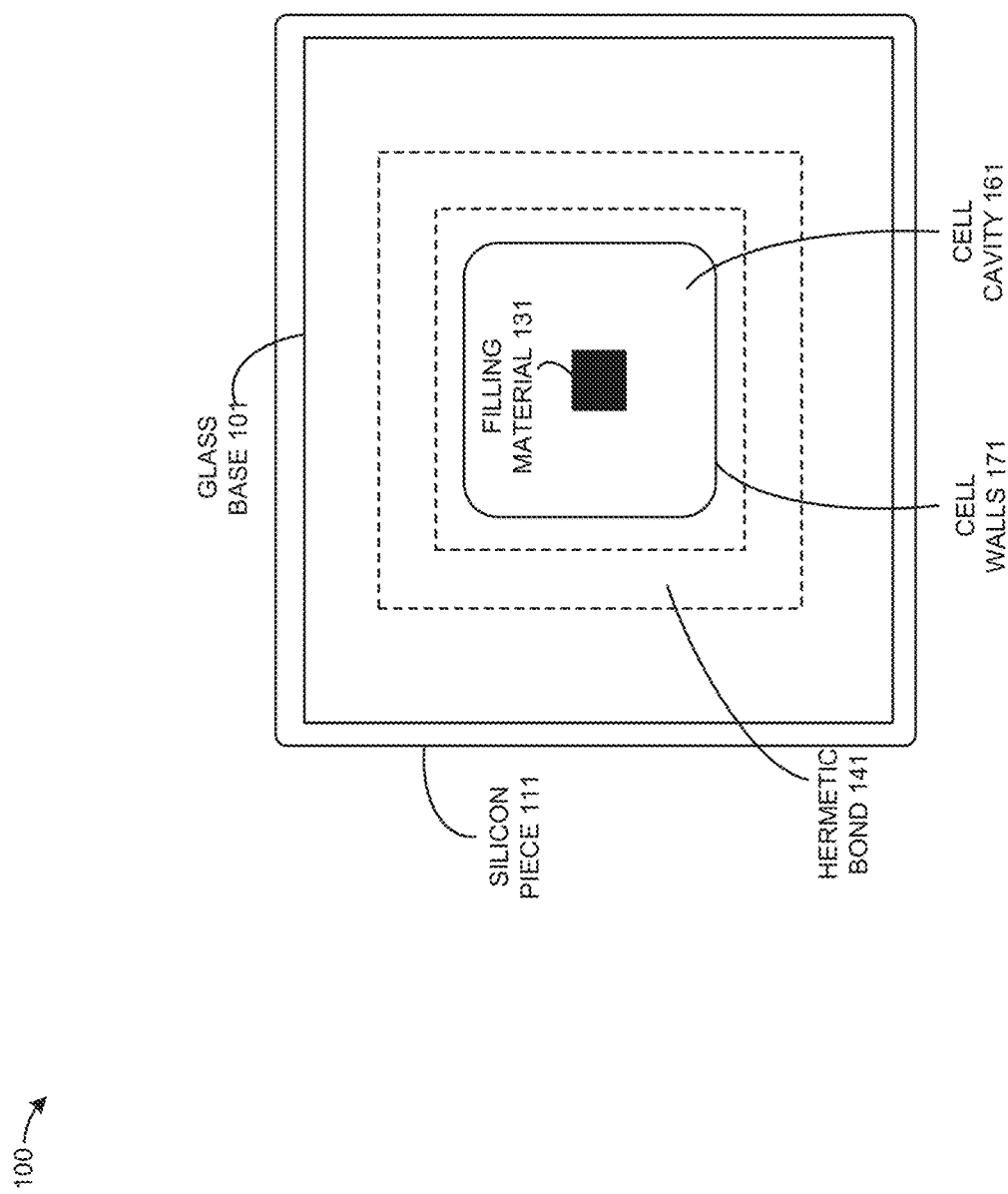
FIG. 2B illustrates an example of a laser bonded glass-silicon vapor cell.

FIGS. 2A and 2B provide additional views of laser bonded glass-silicon vapor cell 100 illustrated in FIG. 1. FIG. 2A illustrates a top-down view of laser bonded glass-silicon vapor cell 100. The top-down view of laser bonded glass-silicon vapor cell 100 comprises silicon piece 111, glass top 121, filling material 131, laser bond 151, cell cavity 161, and cell walls 171. Glass top 121 is positioned above silicon piece 111. Laser bond 151 encircles cell walls 171 and hermetically binds the lower surface of glass top 121 to the upper surface of silicon piece 111.

FIG. 2B illustrates a bottom-up view of laser bonded glass-silicon vapor cell 100. The bottom-up view of laser bonded glass-silicon vapor cell 100 comprises glass base 101, silicon piece 111, filling material 131, hermetic bond 141, cell cavity 161, and cell walls 171. Glass base 101 is positioned below silicon piece 111. Hermetic bond 141 encircles cell walls 171 and hermetically binds the upper surface of glass base 101 to the lower surface of silicon piece 111.

Figure 3:
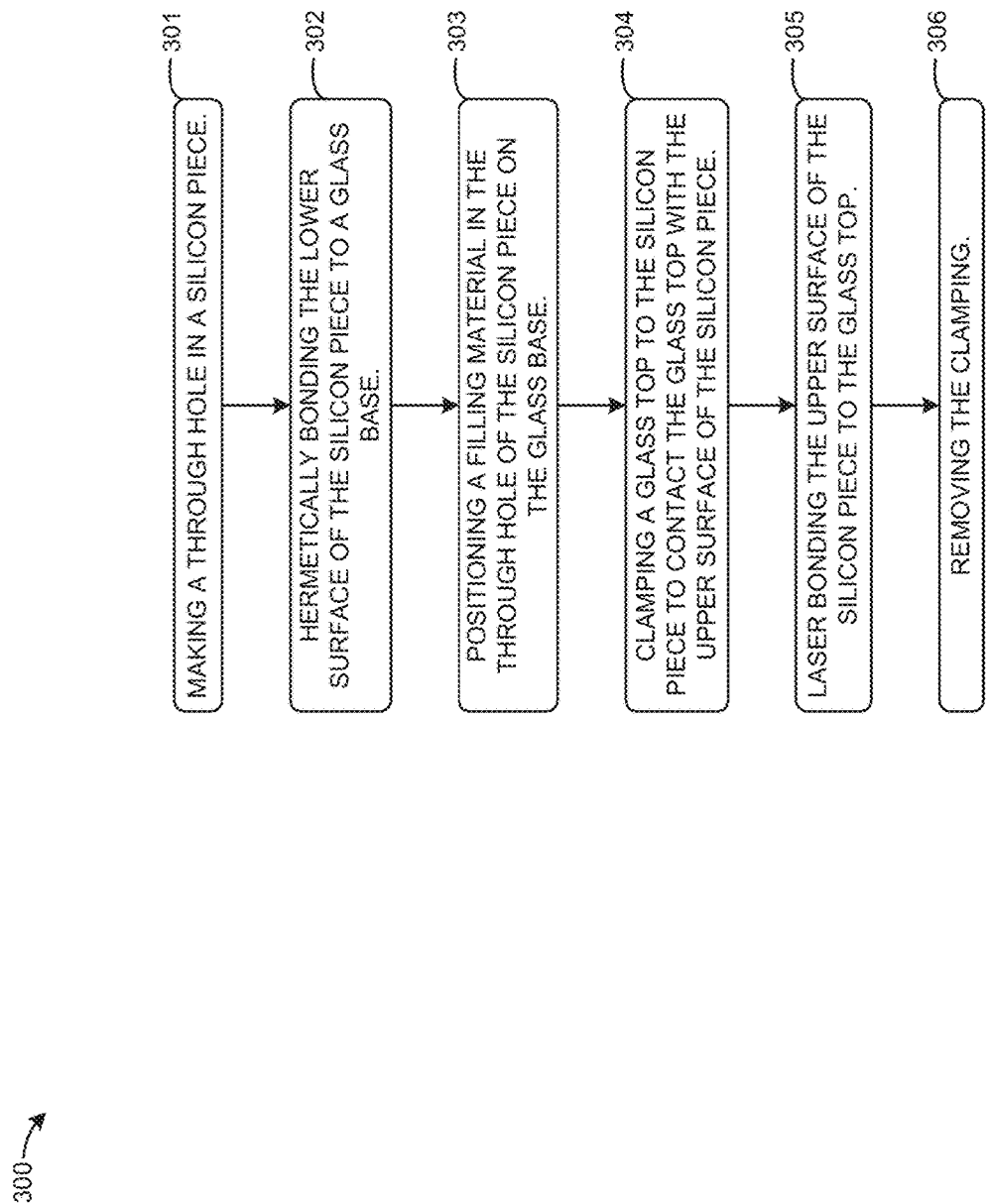
FIG. 3 illustrates an exemplary method of manufacture for a laser bonded glass-silicon vapor cell.

FIG. 3 illustrates process 300. Process 300 comprises a method of manufacturing a laser bonded glass-silicon vapor cell. For example, process 300 may be used to construct laser bonded glass-silicon vapor cell 100 illustrated in FIGS. 1, 2A, and 2B. The structure and operations of process 300 may differ in other examples. The operations of process 300 comprise making a through hole in a silicon piece (step 301). The operations further comprise hermetically bonding the lower surface of the silicon piece to a glass base (step 302). The operations further comprise positioning a filling material in the through hole of the silicon piece on the glass base (step 303). The operations further comprise clamping a glass top to the silicon piece to contact the glass top with the upper surface of the silicon piece (step 304). The operations further comprise laser bonding the upper surface of the silicon piece to the glass top (step 305). The operations further comprise removing the clamping (step 306).

FIGS. 4A-4D illustrate process 400. Process 400 comprises a method of manufacturing a laser bonded glass-silicon vapor cell. For example, process 400 may be used to construct laser bonded glass-silicon vapor cell 100 illustrated in FIGS. 1, 2A, and 2B. Process 400 comprises an example of process 300, however process 300 may differ. In other examples, process 400 may differ.

Figure 4A:
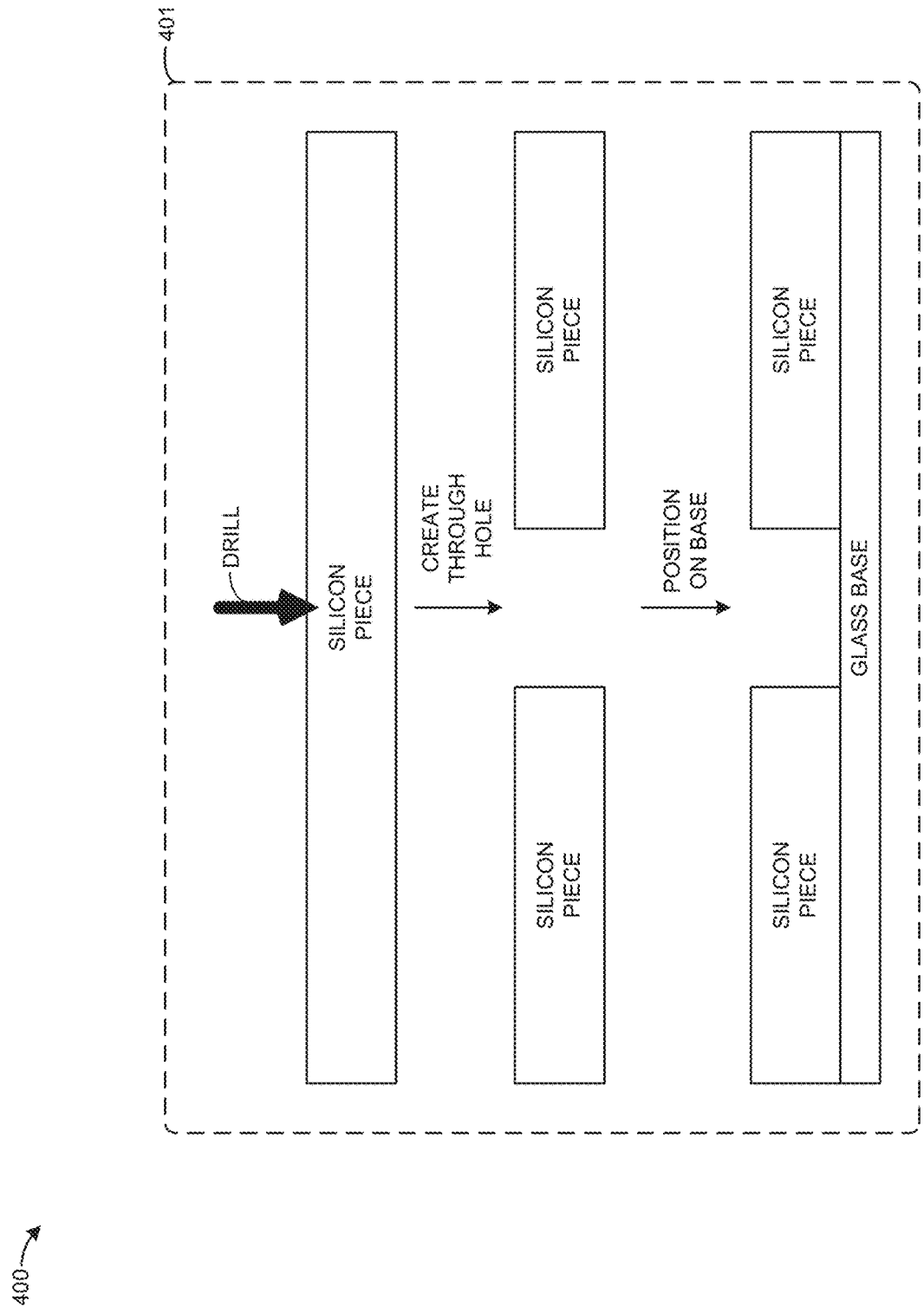
FIG. 4A illustrates an exemplary method of manufacture for a laser bonded glass-silicon vapor cell.

FIG. 4A illustrates process step 401. Process step 401 comprises drilling a silicon piece to create a through hole that transverses the horizontal plane of the silicon piece. For example, a mechanical drill may be lowered onto the silicon piece. The mechanical drill may be turned on and bore a through hole in the silicon piece. In some examples, multiple through holes may be drilled in the silicon piece. The silicon piece is then positioned on a glass base. In some examples, the glass base is also drilled to create an indentation on the upper surface of the glass base. The indentation may be configured to hold a filling material (e.g., filling material 131). In some examples, the silicon piece may be further drilled to create an indentation in the silicon piece alongside the through that is configured to hold a filling material. For example, the indentation in the silicon piece may be made on the through hole walls to create a pocket to hold a filling material.

Figure 4B:
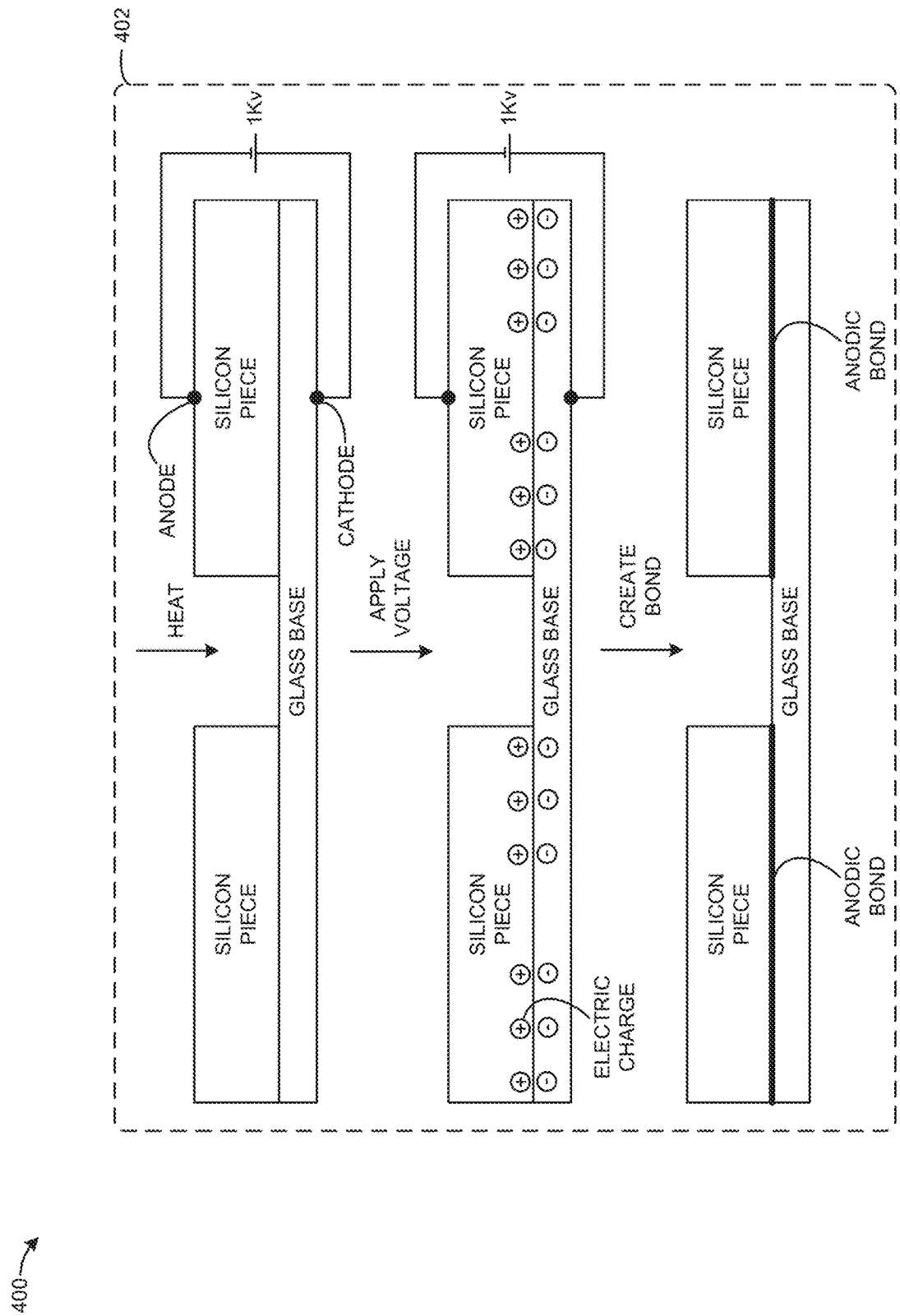
FIG. 4B illustrates an exemplary method of manufacture for a laser bonded glass-silicon vapor cell.

FIG. 4B illustrates process step 402. Process step 402 comprises attaching electrodes to the glass base and the silicon piece. One electrode forms the anode while the other electrode forms the cathode. The anode is attached to the silicon piece and the cathode is attached to the glass base. The electrodes may comprise plates that fully contact the glass base and silicon piece, points electrodes that make point contact with the glass base and silicon piece, and/or patterned electrodes to provide patterned contact with the glass base and silicon piece. For example, the patterned contact may focus bond creation at specific locations on the glass base and silicon piece. The silicon piece and glass base are heated to allow for anodic bonding. For example, the silicon piece and glass base may be heated to 250-400° C. The elevated temperature increases ion mobility within the glass base. The heating may be provided by an oven, hot plate, laser, and/or some other type of heat source. For example, heat can be applied by a laser and anodic bonding can be performed locally to the area heated by the laser and the bond can be expanded as laser is moved. In some examples, pressure is applied to the glass base and the silicon piece to improve contact at the bonding interface. For example, the electrodes may additionally comprise a mechanical clamp to apply the pressure.

When an adequate temperature has been reached (e.g., 300° C.), a voltage source passes an electric current is passed between the anode and the cathode through the silicon piece and glass base. Typically, the electric current is driven by an electric potential of several hundred volts. In this example, the voltage source provides an electric potential of 1000 volts. The electric current causes positively charged ions in the glass base like sodium ($Na^+$) to diffuse towards the cathode and causes negatively charged ions in the glass like oxygen ($O^-$) to diffuse towards the silicon piece. The diffusion of the positively charged ions depletes the bonding surface of the glass base of positive ions allowing the bonding surface to develop a negative area charge. The electric current causes the silicon piece to develop a positive area charge at the bonding surface. The negatively charged ions pass out of the glass base at the bonding surface and react with the silicon piece to create the anodic bond. For example, oxygen ions of the glass base may pass out of the glass base and react with silicon atoms in the silicon piece to form siloxane thereby hermetically bonding the glass base to the silicon piece.

The temperature and voltage are maintained until an anodic bond is formed between the upper surface of the glass base and the lower surface of the silicon piece. Typically, the bonding process takes between 5-20 minutes. Bonding time increases with a decrease in temperature. Bonding time increases with a decrease in voltage. After the bond is formed, the silicon piece and the glass base are cooled, and the electrodes are removed. Once bonded, the upper surface of the glass base is exposed where the through hole in the silicon piece was drilled.

Figure 4C:
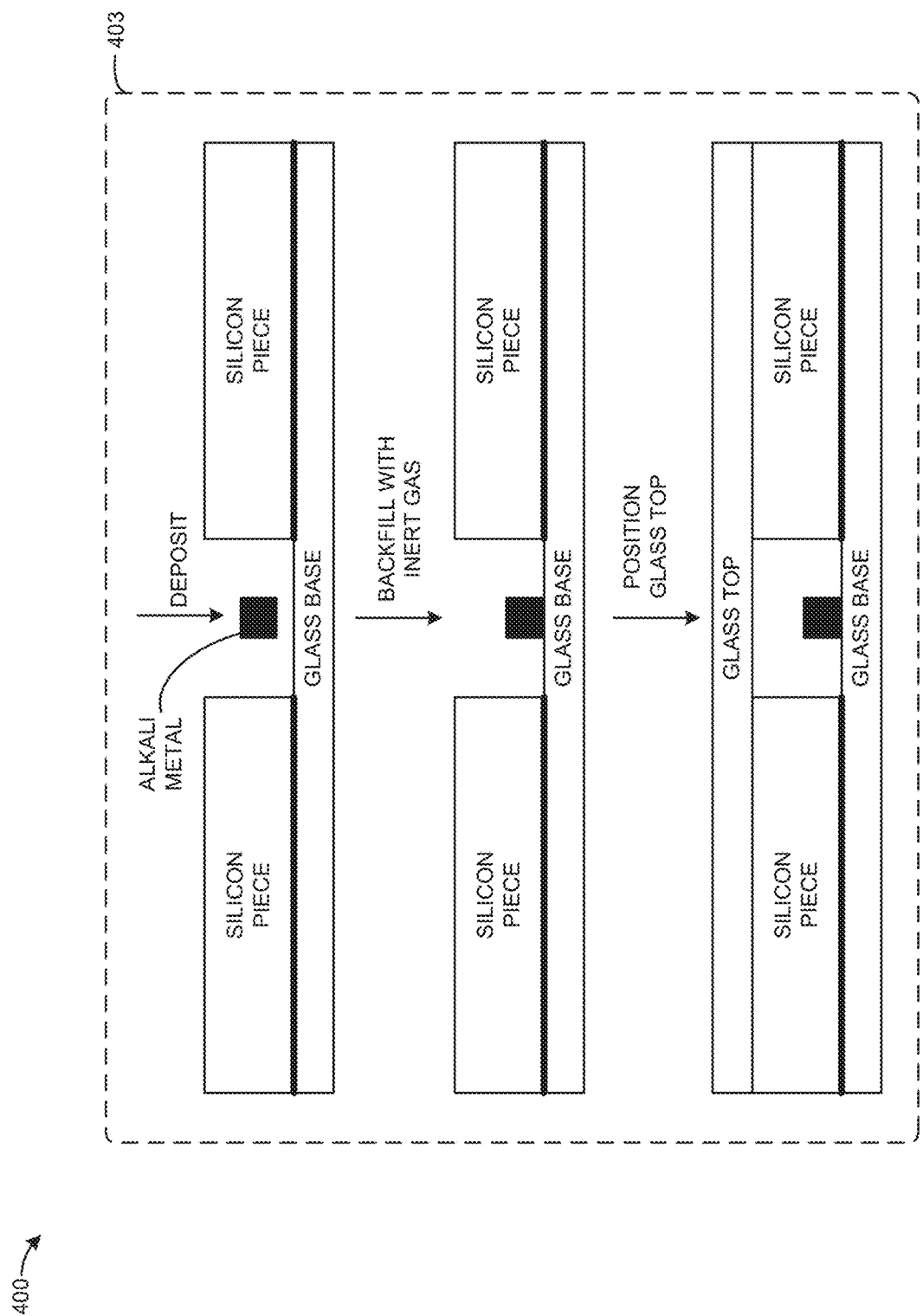
FIG. 4C illustrates an exemplary method of manufacture for a laser bonded glass-silicon vapor cell.

FIG. 4C illustrates process step 403. Process step 403 comprises placing the silicon piece and glass base in an inert environment. For example, the silicon piece and glass base may be placed in a vacuum chamber where a vacuum is drawn to create an inert environment. An alkali metal is deposited through the through hole of the silicon piece onto the upper surface of the glass base. The alkali metal may be deposited on the glass base using a nozzle. The nozzle may be lowered through the through hole in the silicon piece and deposit the alkali metal. In some examples, the exposed regions of the glass base may include indentations to hold the alkali metal. The inert environment inhibits chemical reaction in the alkali metal. The inert environment may comprise a vacuum, a non-reactive gas, or some other type of medium that inhibits chemical reaction of the alkali metal. The alkali metal may comprise a metal like rubidium. In other examples, the alkali metal may instead comprise a salt slush like a rubidium azide mixture.

Once the alkali metal is deposited in the through hole, the through hole is backfilled with inert gas like helium or nitrogen in addition to the alkali metal. Typically, the inert gas does not react, or reacts in only a limited way, with the alkali metal deposits and alkali metal vapor. A glass top is positioned on the upper surface of the silicon piece. The glass top, glass base, and through hole walls of the silicon piece create a cell cavity that fully enclose the alkali metal and the backfilled inert gas. The backfilling creates a desired pressure within the cell cavity. For example, the pressure in the cell cavity may be set to allow a desired amount of the alkali metal to sublimate.

Figure 4D:
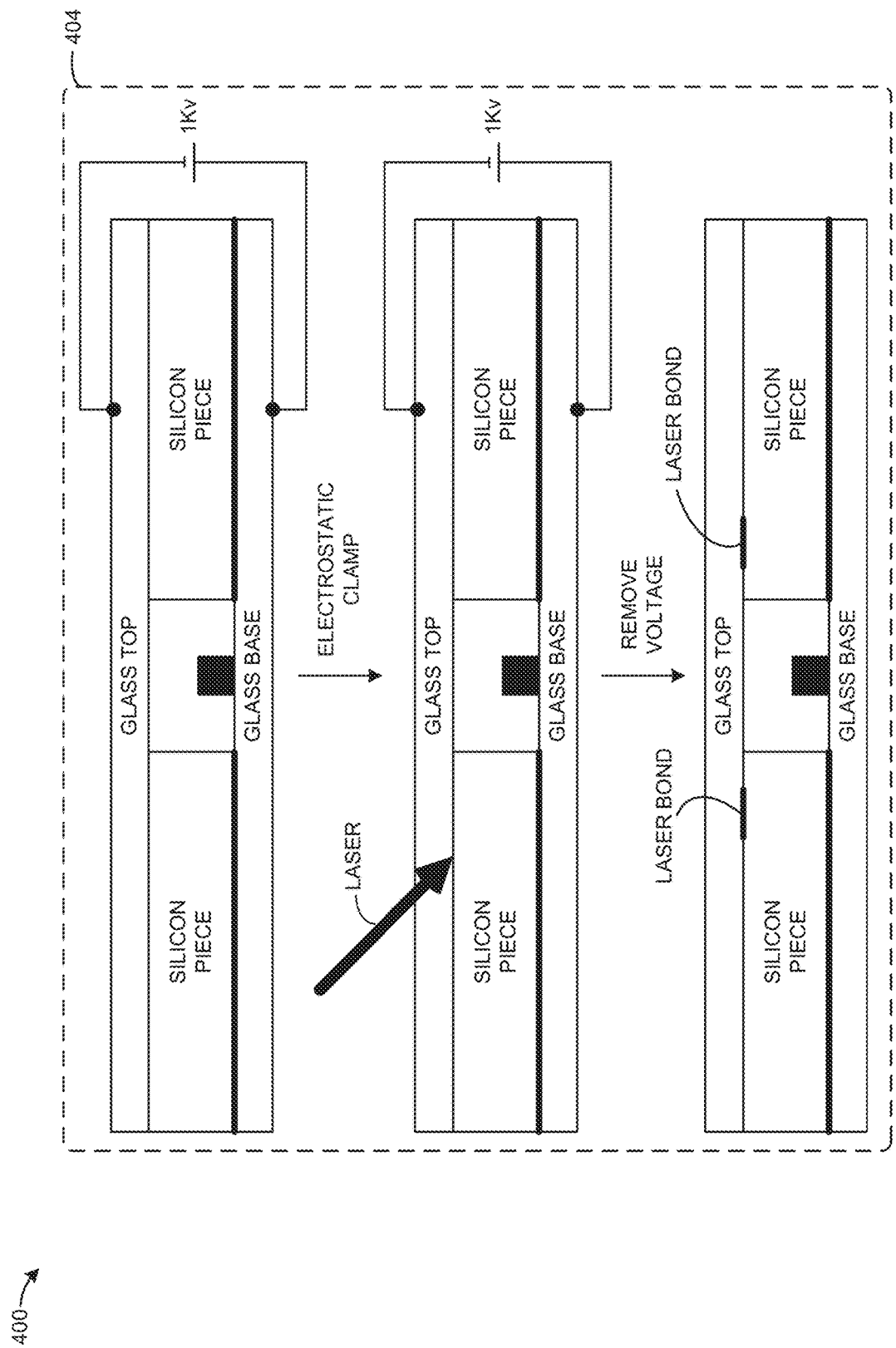
FIG. 4D illustrates an exemplary method of manufacture for a laser bonded glass-silicon vapor cell.

FIG. 4D illustrates process step 404. Process step 404 comprises attaching an electrode to the glass top and the glass base. An electric potential is generated by the voltage source to electrostatically clamp the glass top to the silicon piece. The electric potential induces a charge difference between the gas top and the silicon piece. The charge difference secures the glass top to the silicon piece by electrostatic interactions. In some examples, downward pressure is applied to the upper surface of the glass top and upward pressure is applied to the lower surface of the glass base to secure the glass top to the silicon piece by other means. For example, the glass top may be mechanically clamped to the silicon piece. The mechanical clamp may be patterned to apply pressure to specific points on the glass top. For example, the pressure may be applied by pressure clamping. Pressure clamping comprises increasing the atmospheric pressure in the environment around the glass top, glass base, and silicon piece to secure the glass top to the glass base.

Once the glass is secured to the silicon piece, a laser welding tool bonds the glass top to the upper surface of the silicon piece. For example, the laser welding tool may comprise a solid-state laser or a gas laser. The laser welding tool applies high energy laser light to the glass top and the silicon piece. The laser light locally heats the interface of the glass top and the silicon piece to a critical temperature(s) to create the laser bond. For example, the critical temperature may comprise a melting point and/or a glass transition point. In this example, the heat provided by the laser light creates three distinct bond types to form the laser bond. The first bond type comprises a laser weld. At the critical temperature, the glass top and silicon piece liquefy at the bonding interface and melt into each other to create the laser weld between the glass top and the upper surface of the silicon piece. The second bond type comprises a laser diffusion bond. The heat provided by the laser causes particle diffusion in the glass top and the silicon piece that hermetically joins the upper surface of the silicon piece to the lower surface of the glass top. The third bond type comprises an anodic bond. The heat provided by the laser light and the electric field provided by the electrostatic binding creates an anodic bond between the glass top and the silicon piece in a manner similar to that described in process step 402. The laser light is moved around the through hole to create a laser bond that encircles the through hole. The laser welding tool removes the laser light and the glass top and silicon piece cool. The electrodes are removed from the glass top and the glass base. The interface between the glass top and silicon piece where the laser light was applied solidifies to bind the lower surface of the glass top to the upper surface of the silicon piece. The laser weld, laser diffusion bond, and the anodic bond hermetically bond the glass top and the silicon piece. In some examples, the heat generated by the laser initiates a chemical activation of the alkali metal. For example, the heat supplied by the laser light may initiate a desired chemical reaction in the alkali metal deposits to create the alkali metal vapor.

In other examples, when process step 404 utilizes a mechanical or pressure clamping method to secure the glass top to the glass base and the electric potential is absent, an anodic bond is not formed during laser bonding and the laser bond only comprises the weld bond type and the diffusion bond type. In such cases, once the laser bonding has completed, the glass top and silicon piece may be anodically bonded to reinforce the laser bond. By anodically bonding the glass top to the silicon base after laser bonding is complete, the process can be done outside of the inert environment, the anodic bond reinforces the laser bond, and improves the hermeticity of the laser bonded glass-silicon vapor cell.

Advantageously, process 400 effectively and efficiently constructs laser bonded glass-silicon vapor cells. Moreover, the laser bonding process effectively bonds the glass top to the silicon piece and locally increases the temperature of the laser bonded glass-silicon vapor cell. The locally elevated temperature inhibits undesired chemical reactions from occurring that alter the chemical composition of the alkali vapor. Moreover, the locally elevated temperature effectively inhibits the diffusion of the alkali vapor into the glass top or the glass base. The resulting lack of diffusion effectively maintains cell pressure and inhibits a change in the composition of the glass top and glass base.

Figure 5:
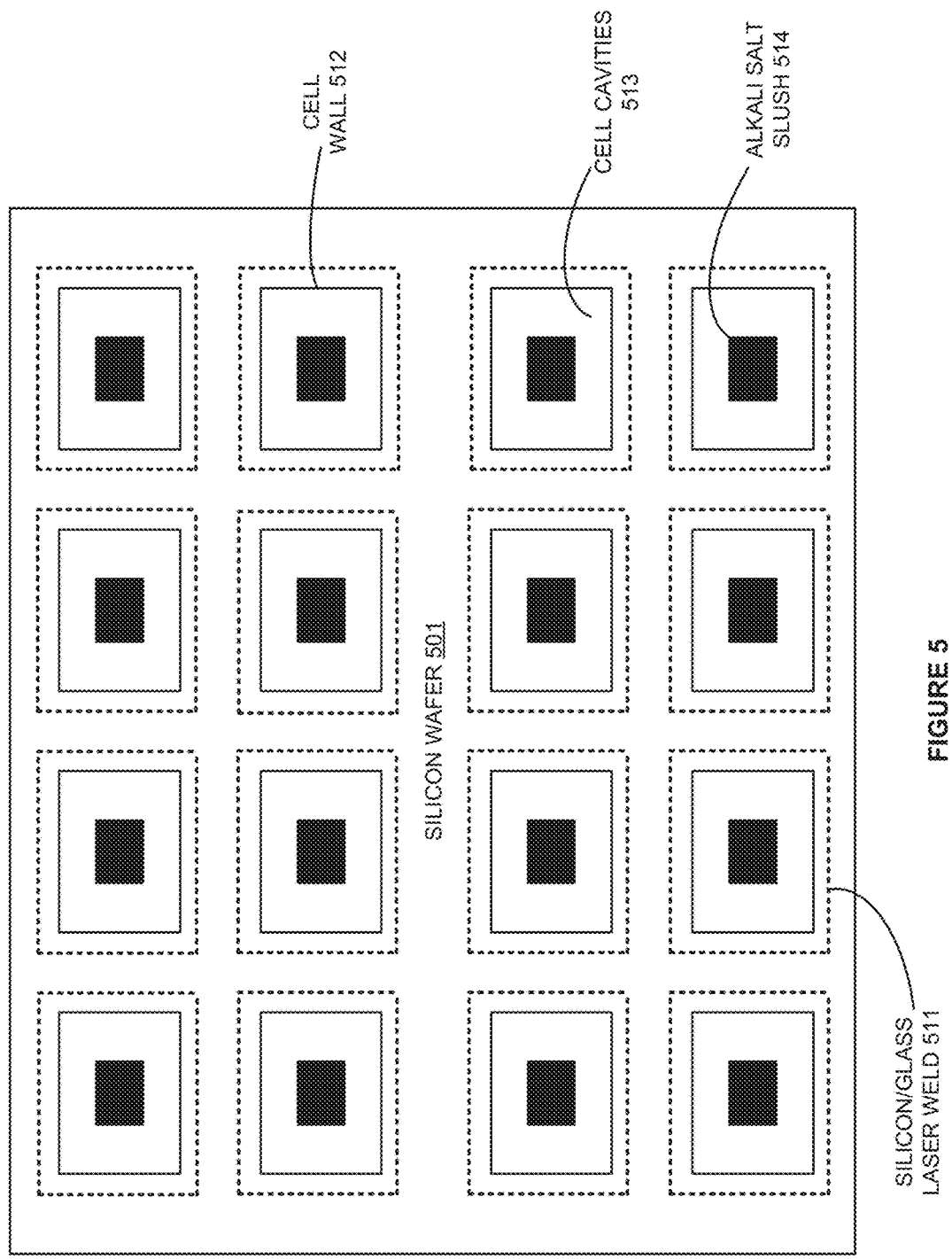
FIG. 5 illustrates an example of laser bonded glass-silicon vapor cells.

FIG. 5 illustrates a top-down view of laser bonded glass-silicon vapor cells 500. Laser bonded glass-silicon vapor cells 500 comprise silicon wafer 501, laser welds 511, cell walls 512, cell cavities 513, and alkali salt slush 514. In this example, silicon wafer 501 is sandwiched between a glass base and a glass top, however the glass base and glass top are omitted for the sake of clarity. Alkali salt slush 514 deposits are positioned in cell cavities 513 on the surface of the glass base and are contained by the glass base, glass top, and cell walls 512. The glass top is bound to silicon wafer 501 by laser welds 511. The laser welds surround cell walls 512 of the through holes hermetically sealing the cell cavities, however other patterns of laser welds may be used in other examples. The alkali deposits release alkali metal vapors that fill cell cavities 513 created by the glass base, glass top, and cell walls 512. The through holes in silicon wafer 501 may be drilled simultaneously allowing for scalable manufacture of laser bonded glass-silicon vapor cells 500. Alkali salt slush deposits may be deposited simultaneously with a patterned nozzle further allowing for scalable manufacture of laser bonded glass-silicon vapor cells 500.

Figure 6:
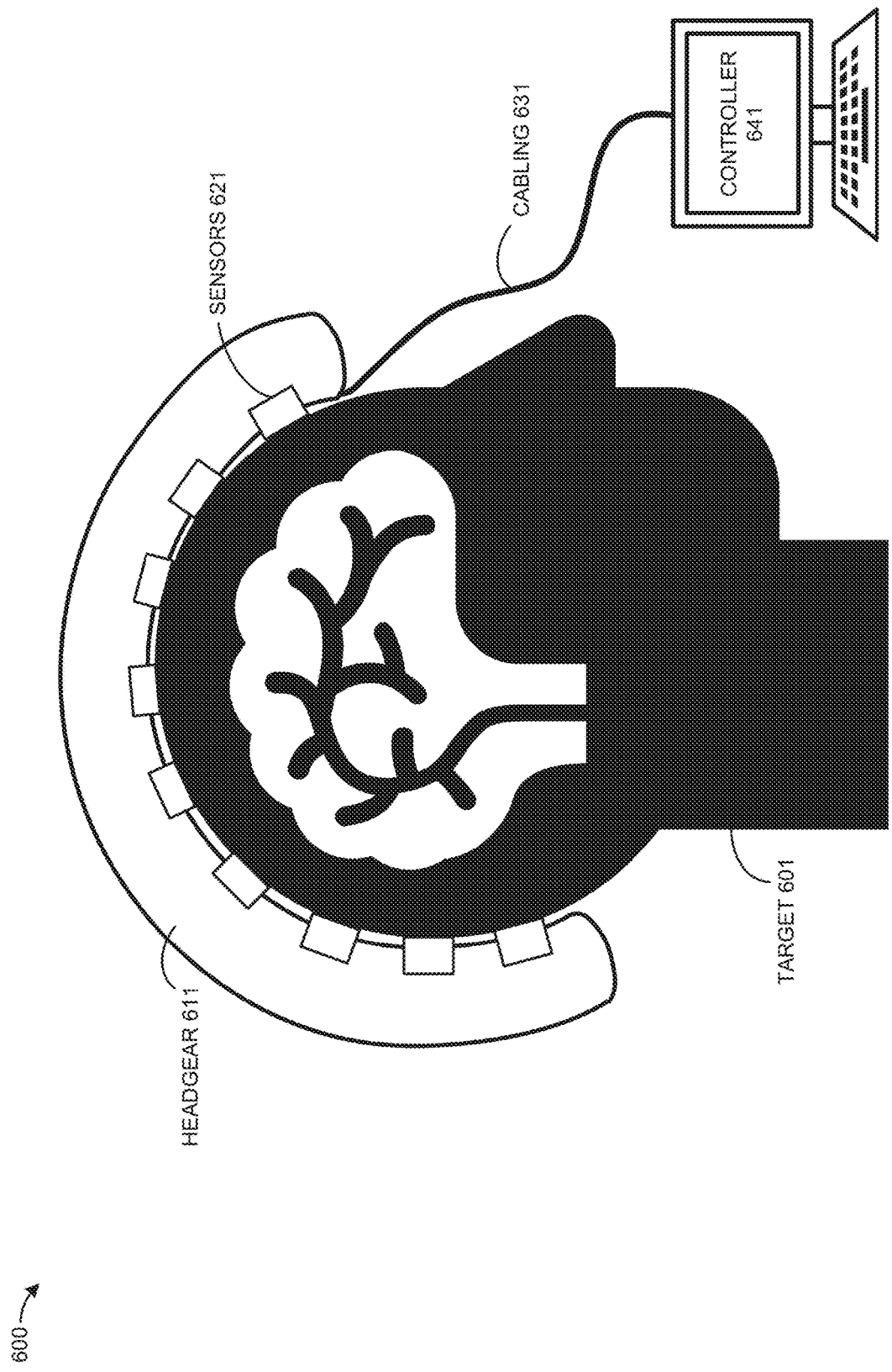
FIG. 6 illustrates an exemplary operational environment for a laser bonded glass-silicon vapor cell.

FIG. 6 illustrates magnetoencephalography environment 600. Environment 600 comprises target 601, headgear 611, sensors 621, cabling 631, and controller 641. Target 601 is depicted as a human brain but may comprise any magnetic field source. Headgear 611 houses sensors 621 and positions sensors 621 proximate to target 601. Headgear 611 may comprise a helmet, flexible cap, or some other type of headgear configured to hold sensors 621. Sensors 621 comprise magnetometer devices configured to detect magnetic fields generated by target 601 and transfer signaling characterizing the magnetic field. For example, sensors 621 may comprise Optically Pumped Magnetometers (OPMs). Sensors 621 comprise components like lasers, coils, laser bonded glass-silicon vapor cells, photo detectors, and heaters. Cabling 631 comprise sheathed metal wires that communicatively couple sensors 621 to controller 641. Controller 641 comprises a computing device configured to process sensor data received from sensors 621. Controller 641 comprises components like processors, memory, transceivers, bus circuitry, and the like. The memory stores software like operating systems, magnetic field modeling applications, modules, and the like. The processors retrieve and execute the software from the memory to drive the operation of controller 641.

Figure 7:
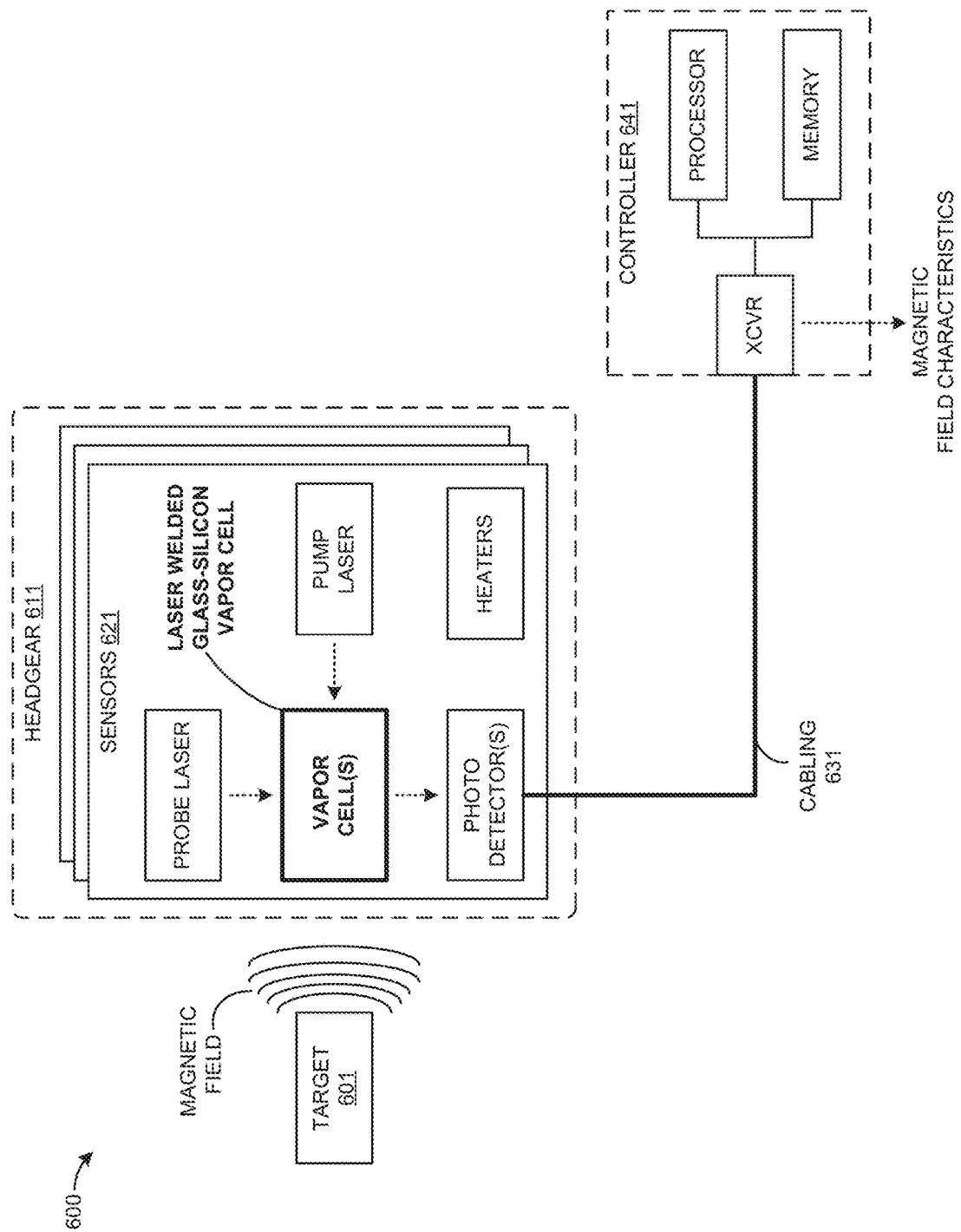
FIG. 7 illustrates an exemplary operational environment for a laser bonded glass-silicon vapor cell.

FIG. 7 illustrates an exemplary operation of magnetoencephalography environment 600. The structure and operation of environment 600 may differ in other examples. In some examples, target 601 is magnetically linked to sensors 621. Sensors 621 are metallically linked to cabling 631 which is metallically and detachably linked to controller 641. Cabling 631 may comprise a ground shield that is coupled to the ground in sensors 621 and to the ground in the in controller 641. Sensors 621 comprise probe lasers, pump lasers, one or more laser bonded glass-silicon vapor cells, photodetectors, coils, and heaters. The pump laser and the probe laser may be combined, or additional lasers may be used. The laser bonded glass-silicon vapor cells comprise fully enclosed cavities that hold alkali metals and/or alkali metal vapors. The laser bonded glass-silicon vapor cells comprise an example of laser bonded glass-silicon vapor cells 100 and 500, however cells 100 and 500 may differ. Sensors 621 may include other electronics like flash circuitry, but they are omitted in this example.

Controller 641 comprises transceiver (XCVR) circuitry, processor circuitry, and memory circuitry. The processor may comprise a Field Programmable Gate Array (FPGA), an Application Specific Integrated Circuit (ASIC), and the like. The memory may comprise flash circuitry, hard drives, and the like. The transceiver circuitry may comprise a pin and socket interface compatible with cabling 631. The processor circuitry, memory circuitry, and transceiver circuitry communicate with one another using bus circuitry. Cabling 631 communicatively couples sensors 621 with controller 641. The processor in controller 641 may write and read sensor operational data to and from the memory. The operational data includes data like sensor ID, configuration parameters, and performance characteristics. For example, the operational data may indicate the number of laser bonded glass-silicon vapor cells, the rubidium level, pressure, build history, and notes for each of sensors 621.

In operation, headgear 611 is secured to the head of target 601 to contact sensors 621 with target 601. Cabling 631 couples to controller 641. Controller 641 reads the memory to identify operational data for sensors 621. Controller 641 processes the operational data to generate control signals for sensors 621. Controller 641 transfers the control signals to sensors 621 over cabling 631.

Sensors 621 operate in response to the control signals from controller 641. Neuronal activity in target 601 generates electromagnetic waves that form a magnetic field. The laser bonded glass-silicon vapor cells are positioned in the magnetic field. The cell cavities of the laser bonded glass-silicon vapor cells hold an alkali metal vapor like rubidium. In some examples, the cell cavities of the glass-silicon vapor cells contain other types of vapors like other alkali vapor types (e.g., cesium), helium, nitrogen-vacancy centers, or vacuum encapsulations. The different types of laser bonded glass-silicon vapor cells could be used instead of, or along with, the alkali metal filled glass-silicon vapor cells in sensors 621. The laser bonded glass-silicon vapor cells are heated by the heaters. The pump laser emits a pump beam that is circularly polarized at a resonant frequency of the vapor to polarize the atoms of the alkali metal vapor. The probe laser emits a probe beam that is linearly polarized at a non-resident frequency of the atoms to probe the atoms of the alkali metal vapor. The probe beam enters the cell cavities of the laser bonded glass-silicon vapor cells where quantum interactions with the atoms in the presence of the target magnetic field alter the energy/frequency of probe beam by amounts that correlate to the magnetic field.

The photodetectors detect the probe beam after these alterations by the vapor atoms. The photodetectors generate and transfer corresponding analog electronic signals that characterize the magnetic field. For example, the corresponding electronic signals may indicate the magnetic field strength at the location of the sensors 621. The photodetectors transfer an electronic signal that carries the magnetic field data over cabling 631 to the controller 641. Controller 641 processes the electronic signal to generate data that more fully characterizes the magnetic field. For example, controller 641 may translate the signals from sensors 621 into magnetic field strengths to characterize the magnetic field. Controller 641 may process sensor data from multiple ones of sensors 621 to model the magnetic field in three dimensions. Controller 641 transfers the magnetic field characteristics to downstream systems.

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof means any connection or coupling, either direct or indirect, between two or more elements; the coupling or connection between the elements can be physical, logical, or a combination thereof. Additionally, the words "herein," "above," "below," and words of similar import, when used in this application, refer to this application as a whole and not to any particular portions of this application. Where the context permits, words in the above Detailed Description using the singular or plural number may also include the plural or singular number, respectively. The word "or" in reference to a list of two or more items, covers all of the following interpretations of the word: any of the items in the list, all of the items in the list, and any combination of the items in the list.

The phrases "in some embodiments," "according to some embodiments," "in the embodiments shown," "in other embodiments," and the like generally mean the particular feature, structure, or characteristic following the phrase is included in at least one implementation of the present technology and may be included in more than one implementation. In addition, such phrases do not necessarily refer to the same embodiments or different embodiments.

The above Detailed Description of examples of the technology is not intended to be exhaustive or to limit the technology to the precise form disclosed above. While specific examples for the technology are described above for illustrative purposes, various equivalent modifications are possible within the scope of the technology, as those skilled in the relevant art will recognize. For example, while processes or blocks are presented in a given order, alternative implementations may perform routines having steps, or employ systems having blocks, in a different order, and some processes or blocks may be deleted, moved, added, subdivided, combined, and/or modified to provide alternative or subcombinations. Each of these processes or blocks may be implemented in a variety of different ways. Also, while processes or blocks are at times shown as being performed in series, these processes or blocks may instead be performed or implemented in parallel or may be performed at different times. Further any specific numbers noted herein are only examples: alternative implementations may employ differing values or ranges.

The teachings of the technology provided herein can be applied to other systems, not necessarily the system described above. The elements and acts of the various examples described above can be combined to provide further implementations of the technology. Some alternative implementations of the technology may include not only additional elements to those implementations noted above, but also may include fewer elements.

These and other changes can be made to the technology in light of the above Detailed Description. While the above description describes certain examples of the technology, and describes the best mode contemplated, no matter how detailed the above appears in text, the technology can be practiced in many ways. Details of the system may vary considerably in its specific implementation, while still being encompassed by the technology disclosed herein. As noted above, particular terminology used when describing certain features or aspects of the technology should not be taken to imply that the terminology is being redefined herein to be restricted to any specific characteristics, features, or aspects of the technology with which that terminology is associated. In general, the terms used in the following claims should not be construed to limit the technology to the specific examples disclosed in the specification, unless the above Detailed Description section explicitly defines such terms. Accordingly, the actual scope of the technology encompasses not only the disclosed examples, but also all equivalent ways of practicing or implementing the technology under the claims.

To reduce the number of claims, certain aspects of the technology are presented below in certain claim forms, but the applicant contemplates the various aspects of the technology in any number of claim forms. For example, while only one aspect of the technology is recited as a method claim, other aspects may likewise be embodied as an apparatus claim, or in other forms, such as being embodied in a means-plus-function claim. Any claims intended to be treated under 35 U.S.C. § 112(f) will begin with the words "means for" but use of the term "for" in any other context is not intended to invoke treatment under 35 U.S.C. § 112(f). Accordingly, the applicant reserves the right to pursue additional claims after filing this application to pursue such additional claim forms, in either this application or in a continuing application.

What is claimed is:

1. A vapor cell, the vapor cell comprising:
    a cell body comprising a through hole;
    a first transparent piece attached to the cell body;
    a second transparent piece laser bonded to the cell body; and
    a filling material positioned in a cavity formed by the through hole, the first transparent piece, and the second transparent piece.

2. The vapor cell of claim 1 wherein the filling material comprises rubidium.

3. The vapor cell of claim 1 wherein the filling material comprises cesium.

4. The vapor cell of claim 1 wherein the filling material comprises nitrogen.

5. The vapor cell of claim 1 wherein the filling material comprises helium.

6. The vapor cell of claim 1 wherein the filling material comprises an alkali salt and azide mixture.

7. The vapor cell of claim 1 wherein:
    the cell body comprises silicon; and
    the first transparent piece and the second transparent piece comprise glass.

8. A method of manufacturing a vapor cell, the method comprising:
    attaching a first transparent piece to a cell body comprising a through hole;
    depositing a filling material into the through hole of the cell body; and
    laser bonding a second transparent piece to the cell body to enclose the filling material.

9. The method of manufacturing of claim 8 wherein depositing the filling material into the through hole comprises depositing the filling material into the through hole and backfilling the through hole with a gas.

10. The method of manufacturing of claim 9 wherein the filling material comprises rubidium and the gas comprises nitrogen.

11. The method of manufacturing of claim 9 wherein the filling material comprises cesium and the gas comprises nitrogen.

12. The method of manufacturing of claim 9 wherein the filling material comprises an alkali salt and azide mixture and the gas comprises nitrogen.

13. The method of manufacturing of claim 8 wherein:
    the cell body comprises a silicon wafer;
    the first transparent piece comprises a first glass piece; and
    the second transparent piece comprises a second glass piece.

14. The method of manufacturing of claim 8 further comprising:
    using a drilling tool to make the through hole in the cell body; and wherein:
    attaching the first transparent piece to the cell body comprises using an anodic bonding tool to attach the first transparent piece to the cell body;
    depositing the filling material comprises using a nozzle to deposit the filling material into the through hole of the cell body; and
    laser bonding the second transparent piece to the cell body comprises using a laser welding tool to laser bond the second transparent piece to the cell body.

15. An apparatus, the apparatus comprising:
    a glass-silicon vapor cell comprising a silicon piece with a through hole, a glass base hermetically bonded to the silicon piece, a glass top laser bonded to the silicon piece, and a filing material positioned in a cavity formed by the through hole, the glass base, and the glass top;
    a heater configured to heat the filling material;
    a laser configured to emit a beam through the glass-silicon vapor cell; and
    a photodetector configured to detect the beam after the beam has passed through the glass-silicon vapor cell.

16. The apparatus of claim 15 wherein the apparatus comprises an atomic spectroscopy device.

17. The apparatus of claim 15 wherein the apparatus comprises a molecular spectroscopy device.

18. The apparatus of claim 15 wherein the apparatus comprises a magnetometer.

19. The apparatus of claim 15 wherein the apparatus comprises an Optically Pumped Magnetometer (OPM).

20. The apparatus of claim 15 wherein the apparatus comprises a Magnetoencephalography (MEG) device.

* * * * *